United States Patent
Hironaka et al.

(10) Patent No.: US 9,273,264 B2
(45) Date of Patent: Mar. 1, 2016

(54) ESTER COMPOUND, LUBRICANT BASE OIL, LUBRICANT, GREASE BASE OIL, AND GREASE

(75) Inventors: Yoshio Hironaka, Kudamatsu (JP); Hiroki Sekiguchi, Sodegaura (JP)

(73) Assignee: IDEMITSU KOSAN CO., LTD., Tokyo (JP)

( * ) Notice: Subject to any disclaimer, the term of this patent is extended or adjusted under 35 U.S.C. 154(b) by 220 days.

(21) Appl. No.: 14/008,890

(22) PCT Filed: Mar. 23, 2012

(86) PCT No.: PCT/JP2012/057509
§ 371 (c)(1),
(2), (4) Date: Sep. 30, 2013

(87) PCT Pub. No.: WO2012/133183
PCT Pub. Date: Oct. 4, 2012

(65) Prior Publication Data
US 2014/0018563 A1    Jan. 16, 2014

(30) Foreign Application Priority Data

Mar. 30, 2011 (JP) ................. 2011-075879
Mar. 30, 2011 (JP) ................. 2011-075880

(51) Int. Cl.
*C07C 59/00* (2006.01)
*C10M 105/34* (2006.01)
*C10M 105/38* (2006.01)

(52) U.S. Cl.
CPC ........... *C10M 105/34* (2013.01); *C10M 105/38* (2013.01); *C10M 2207/2835* (2013.01); *C10N 2230/02* (2013.01); *C10N 2240/02* (2013.01); *C10N 2250/10* (2013.01)

(58) Field of Classification Search
CPC ............ C10M 105/34; C10M 105/38; C10M 2207/2835; C10M 2230/02; C10M 2240/02; C10M 2250/10
USPC ....................................... 554/213
See application file for complete search history.

(56) References Cited

U.S. PATENT DOCUMENTS 5,639,791 A    6/1997  O'Lenick, Jr.
2007/0282123 A1  12/2007  Sato et al.

FOREIGN PATENT DOCUMENTS

EP    1 060 740 A1    12/2000
EP    1 710 225 A1    10/2006
(Continued)

OTHER PUBLICATIONS

International Search Report issued Jun. 19, 2012 in Application No. PCT/JP2012/057509.
(Continued)

*Primary Examiner* — Deborah D Carr
(74) *Attorney, Agent, or Firm* — Oblon, McClelland, Maier & Neustadt, L.L.P.

(57) ABSTRACT

An ester compound is represented by the following formula (1).

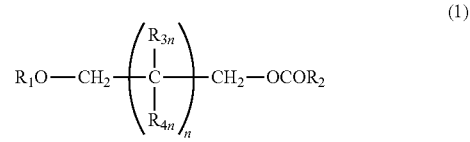

In the formula: $R_1$ and $R_2$ each independently represent an alkyl group having 5 to 18 carbon atoms; $R_{3n}$ represents a hydrogen atom or an alkyl group having at most 5 carbon atoms; $R_{4n}$ represents hydrogen or $CH_2OR_{5n}$; $R_{5n}$ represents an alkyl group having 5 to 18 carbon atoms; and n represents an integer of 1 to 3.

15 Claims, 8 Drawing Sheets

(56) References Cited

FOREIGN PATENT DOCUMENTS

| JP | 59055853 | * | 3/1984 |
| JP | 3-155108 A | | 7/1991 |
| JP | 11-181457 | | 7/1999 |
| JP | 2001-31611 A | | 2/2001 |
| JP | 2001-107066 | | 4/2001 |
| JP | 2003-321691 | | 11/2003 |
| JP | 2005-343858 A | | 12/2005 |
| JP | 2007-39496 | | 2/2007 |
| JP | 2007-204451 A | | 8/2007 |
| JP | 2007204451 A | * | 8/2007 |
| JP | 2008-179773 | | 8/2008 |
| JP | 2010-275471 | | 12/2010 |

OTHER PUBLICATIONS

International preliminary Report on Patentability and Written Opinion issued Oct. 8, 2013 in Application No. PCT/JP2012/057509.

W. J. Baumann, et al., "Alkoxylipids IV. Synthesis and Characterization of Naturally Occurring Ethers, Esters and Ether Esters of Diols", Biochimica et Biophysica Acta, Lipids and Lipid Metabolism, vol. 144, No. 2, 1967, pp. 355-365.

Shipeng Guo, et al., "Direct Conversion of Sunflower Shells to Alkanes and Aromatic Compounds", Energy and Fuels, vol. 22, No. 5, Aug. 8, 2008 (published on web), pp. 3517-3522.

Souad El-Gengaihi, et al., "In vivo and in vitro comparative studies of *Origanum* species", Journal of Food, Agriculture & Environment, vol. 4 (3 & 4), 2006, pp. 127-134.

Chunbao Xu, et al., Liquefaction of Corn Distillers Dried Grains with Solubles (DDGS) in Hot-Compressed Phenol, BioResources vol. 3, No. 2, 2008, pp. 363-382.

Combined Chinese Office Action and Search Report issued Apr. 16, 2015 in Patent Application No. 201280015735.0 ( with English language translation and English translation of Category of Cited Documents).

STN Columbus, http://www.cas.org/training /stn/database-specific, CPCH1362308P, Feb. 25, 1994, pp. 1-10.

Combined Chinese Office Action and Search Report issued Aug. 11, 2014 in Patent Application No. 201280015735.0 (with English translation and English translation of categories of cited documents).

Extended European Search Report issued Aug. 28, 2014 in Patent Application No. 12764532.3.

Zhu Bin-chao, et al., "GC determination of fatty acids in fermented slurry from steamed sponge cake" Food Science and Technology, vol. 35, No. 11, 2010, pp. 309-311 (with English Abstract).

Fátima Aparicio, et al., "Amplification of chirality in $N, N'$-1,2-ethanediylbisbenzamides: from planar sheets to twisted ribbons" Chem Commun, vol. 46, 2010, pp. 8356-8358.

Subash C. Jonnalagadda, et al., "Synthesis of α-carboranyl-α-acyloxy-amides as potential BNCT agents" Tetrahedron Lett.,vol. 50, No. 30, Jul. 29, 2009, pp. 4314-4317.

Hiroyuki Yoshida, et al., "Synthesis of Sulfated Cerebroside Analogs Having Mimicks of Ceramide and Their Anti-human Immunodeficiency Virus Type 1 Activities" Chemical & Pharmaceutical Bulletin, vol. 43, No. 4, 1995, pp. 594-602.

* cited by examiner

ESTER COMPOUND, LUBRICANT BASE OIL, LUBRICANT, GREASE BASE OIL, AND GREASE

TECHNICAL FIELD

The present invention relates to an ester compound and lubricant base oil, lubricant, grease base oil, and grease, each of which including or provided by blending the ester compound.

BACKGROUND ART

Lubricant is used in a wide temperature range from low temperatures to high temperatures. Accordingly, lubricant exhibiting a high viscosity index and a good low-temperature fluidity is required for a fluid dynamic bearing and an oil-impregnated bearing which are used in a motor such as a hard disk drive. Moreover, grease base oil exhibiting a high viscosity index and a good low-temperature fluidity is also required for grease used in a wide temperature range from low temperatures to high temperatures.

In response to such needs, various base oils have been proposed. For instance, a predetermined diester base oil exhibiting both of a high viscosity index and a low-temperature fluidity has been proposed to be used for lubricant and grease (see, for instance, Patent Literatures 1 to 3).

CITATION LIST

Patent Literature(s)

Patent Literature 1: JP-A-2003-321691
Patent Literature 2: JP-A-2010-275471
Patent Literature 3: JP-A-2007-039496

SUMMARY OF THE INVENTION

Problems to be Solved by the Invention

However, it is difficult to provide lubricant and grease sufficiently satisfying both of a high viscosity index and a low-temperature fluidity even using the base oils disclosed in Patent Literatures 1 to 3.

An object of the invention is to provide a compound exhibiting a high viscosity index and an excellent low-temperature fluidity, lubricant base oil and grease base oil, each of which including or provided by blending the compound, lubricant using the lubricant base oil and grease using the grease base oil.

Means for Solving the Problems

In order to solve the above-described problems, the invention provides an ester compound, lubricant base oil, lubricant, grease base oil and grease as follows.
(1) An ester compound represented by the following formula (1).

[Formula 1]

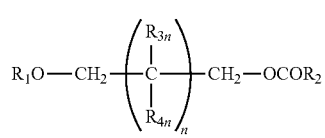

In the formula: $R_1$ and $R_2$ each independently represent an alkyl group having 5 to 18 carbon atoms; $R_{3n}$ represents hydrogen or an alkyl group having at most 5 carbon atoms; $R_{4n}$ represents hydrogen or $CH_2OR_{5n}$, $R_{5n}$ representing an alkyl group having 5 to 18 carbon atoms; and n represents an integer of 1 to 3.
(2) The aforementioned ester compound of the formula (1) which is an alkyldietheralkylmonoester compound of trimethylolalkane represented by the following formula (2).

[Formula 2]

In the formula: R and R' each independently represent an alkyl group having 5 to 18 carbon atoms; and R" represents hydrogen or an alkyl group having at most 5 carbon atoms.
(3) The aforementioned ester compound having total carbon atoms of 24 to 42.
(4) The aforementioned ester compound, in which the trimethylolalkane is trimethylolpropane or trimethylolethane.
(5) Lubricant base oil including or provided by blending the aforementioned ester compound.
(6) Lubricant including or provided by blending the aforementioned lubricant base oil.
(7) The aforementioned lubricant used for an oil-impregnated bearing or a fluid dynamic bearing.
(8) Grease base oil including or provided by blending the aforementioned ester compound.
(9) Grease including or provided by blending the grease base oil.
(10) The aforementioned ester compound represented by the formula (1) which is an alkylmonoetheralkylmonoester compound of 2,4-diethyl-1,5-pentanediol represented by the following formula (3).

[Formula 3]

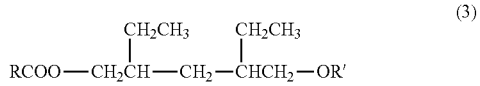

In the formula: R and R' independently represent an alkyl group having 5 to 18 carbon atoms; and the compound has total carbon atoms of 24 to 40.
(11) Lubricant base oil including or provided by blending the aforementioned ester compound.
(12) Lubricant including the aforementioned lubricant base oil.
(13) The aforementioned lubricant used for an oil-impregnated bearing or a fluid dynamic bearing.
(14) Grease base oil including or provided by blending the aforementioned ester compound.
(15) Grease including the grease base oil.
(16) A manufacturing intermediate of the aforementioned ester compound, the manufacturing intermediate being represented by the following formula (4).

[Formula 4]

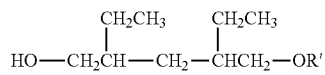
(4)

In the formula, R' represents an alkyl group having 5 to 18 carbon atoms.

The novel ester compound of the invention exhibits a high viscosity index and an excellent low-temperature fluidity. Accordingly, the ester compound is useful as base oil of lubricant and is suitably usable as lubricant for an oil-impregnated bearing or a fluid dynamic bearing. Moreover, the ester compound is also useful as grease base oil and grease including or provided by blending the grease base oil.

DESCRIPTION OF EMBODIMENT(S)

Figure 1:
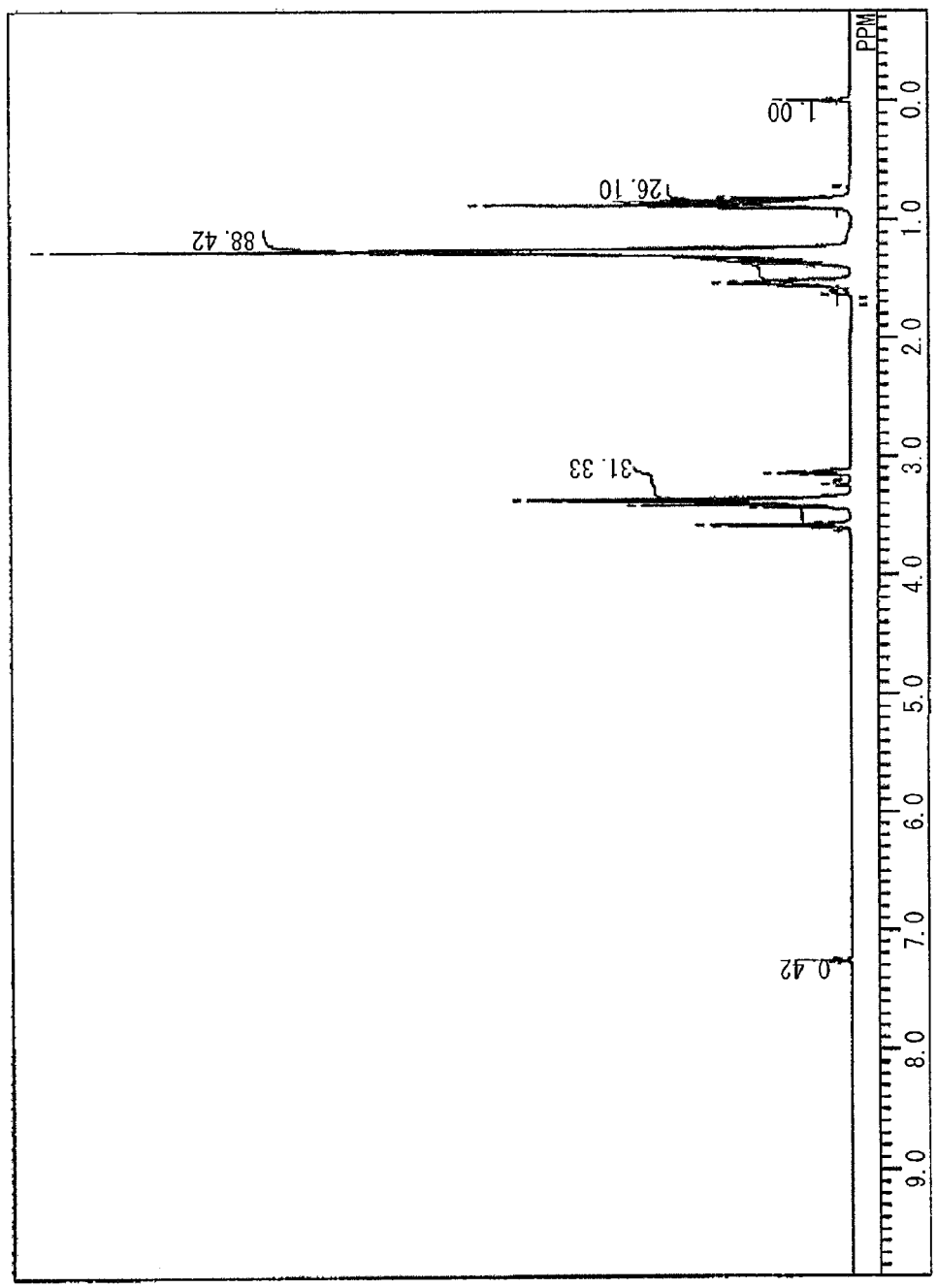
FIG. 1 shows a $^1$HNMR chart of 2,2-bis(nonyloxymethyl)butane-1-ol (intermediate) in Example 1.

An ester compound of the invention is represented by the following formula (1).

[Formula 5]

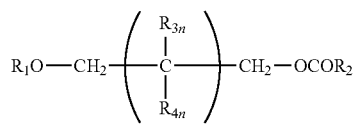
(1)

In the formula, $R_1$ and $R_2$ each independently represent an alkyl group having 5 to 18 carbon atoms. $R_{3n}$ represents hydrogen or an alkyl group having at most 5 carbon atoms. $R_{4n}$ represents hydrogen or $CH_2OR_{5n}$, where $R_{5n}$ represents an alkyl group having 5 to 18 carbon atoms. n represents an integer of 1 to 3.

A first exemplary embodiment and a second exemplary embodiment of the invention will be described in more detail.

First Exemplary Embodiment

An ester compound in the first exemplary embodiment is an alkyldietheralkylmonoester compound of trimethylolalkane represented by the following formula (2).

[Formula 6]

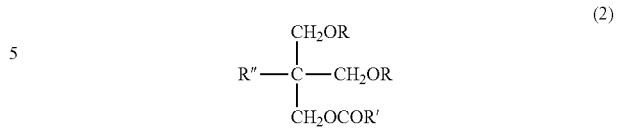
(2)

In the formula (2), R and R' independently represent an alkyl group having 5 to 18 carbon atoms. When the number of the carbon atoms of the alkyl group R is 4 or less, a viscosity index may be decreased.

On the other hand, when the number of the carbon atoms of the alkyl group R is 19 or more, kinematic viscosity may be increased to deteriorate fluidity in a low temperature region, occasionally resulting in solidification. Accordingly, the alkyl group R preferably has 8 to 16 carbon atoms.

When the number of the carbon atoms of the alkyl group R' is 4 or less, a viscosity index may be decreased. When hydrolysis occurs by any chance, short-chain fatty acid may be generated to cause corrosion. On the other hand, when the number of the carbon atoms of the alkyl group R' is 19 or more, kinematic viscosity may be increased to deteriorate fluidity in a low temperature region, occasionally resulting in solidification. Accordingly, the alkyl group W particularly preferably has 8 to 16 carbon atoms.

Herein, R" represents hydrogen or an alkyl group having at most 5 carbon atoms, among which an alkyl group having 1 or 2 carbon atoms is preferable. In other words, a structure of trimethylolalkane of the formula (2) is preferably a structure of trimethylolethane or trimethylolpropane. When R" has 6 carbon atoms or more, kinematic viscosity may be increased. Moreover, availability of a material for such R" is low.

Although the aforementioned alkyl groups are preferably linear for improvement in the viscosity index, the alkyl groups may be branched as long as advantages of the invention are not hampered.

The total carbon atoms of the compound of the formula (2) are preferably in a range of 24 to 42. When the total carbon atoms are 23 or less, the viscosity index may be decreased and vaporizability in a high temperature region may be increased. On the other hand, when the total carbon atoms are 43 or more, the kinematic viscosity may be increased to deteriorate fluidity in a low temperature region, occasionally resulting in solidification. Accordingly, the total carbon atoms are particularly preferably in a range of 26 to 36.

The aforementioned compound of the formula (2) can be easily manufactured, for instance, through an intermediate represented by the following formula (5).

[Formula 7]

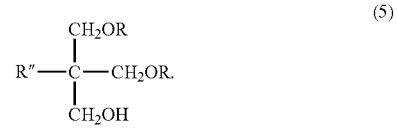
(5)

In the formula, R and R" represent the same as those in the formula (2).

The intermediate represented by the formula (2) can be manufactured by heating trimethylolalkane and alkyl bromide with stirring in a concentrated alkali solution in the presence of a phase transfer catalyst. Preferable reaction conditions and identification method are as follows:

Temperature: 40 to 95 degrees C. (more preferably 60 to 80 degrees C.);
Time: 1 to 24 hours (preferably about 8 hours);
Catalyst: phase transfer catalyst (tetrabutyl ammonium bromide, tetraisopropyl ammonium bromide and the like);
Solvent: aqueous sodium hydroxide of a concentration of 48 mass % or more, to which solid sodium hydroxide may be added during reaction; and
Identification: transition of the reaction can be checked by gas chromatography.

The structure can be identified in more detail by mass analysis, NMR analysis, IR analysis and the like.

A mixture of monoether, diether and triether obtained by the above method is subjected to distilled separation to obtain diether (intermediate, the formula (5)). The diether is used in manufacturing the compound of the formula (2). Specifically, the diether and alkyl carboxylic acid are heated with stirring in the presence of an acid catalyst to perform an esterification reaction, in which the generated water only needs to be eliminated.

Moreover, the compound (2) of the formula (2) can also be obtained in a good yield by reacting the diether (diether monoalcohol) and alkyl carboxylic acid chloride in the presence of a base at the room temperature.

Although both of the compounds obtained in the reaction include impurities, the compounds can be preferably used as lubricant base oil or grease base oil by being subjected to distillation.

Two preferable examples of the esterification reaction of diether monoalcohol are described as follows.

Reaction of Diether Monoalcohols (the Formula (5)) and Alkyl Carboxylic Acid
Temperature: 100 to 190 degrees C. (preferably 120 to 180 degrees C.);
Time: 1 to 24 hours (more preferably about 8 hours);
Catalyst: sulfuric acid, titanic acid tetrabutyl, titanic acid tetraisopropyl and titanic acid tetraethyl;
Solvent: toluene, xylene, trimethylbenzene and the like;
Reactor: dehydration using a Dean-Stark apparatus
Identification: transition of the reaction can be checked by gas chromatography.

The structure can be identified by mass analysis, NMR analysis, IR analysis and the like.

Reaction of Diether Monoalcohol (the Formula (5)) and Alkyl Carboxylic Acid Chloride
Temperature: 10 to 60 degrees C. (more preferably 20 to 40 degrees C.);
Time: 1 to 24 hours (more preferably about 4 hours);
Base: N,N-dimethylaniline, triethylamine and the like;
Solvent: tetrahydrofuran, dibutylether, dimethylether and the like;
Identification: transition of the reaction can be checked by gas chromatography.

The structure can be identified by mass analysis, NMR analysis, IR analysis and the like.

The aforementioned compound of the formula (2) exhibits a high viscosity index and an excellent low-temperature fluidity. Accordingly, the compound of the formula (2) is useful as base oil of lubricant and is suitably usable as lubricant for an oil-impregnated bearing or an fluid dynamic bearing. Moreover, the compound of the formula (2) is also useful as grease base oil and grease including or provided by blending the grease base oil.

When the compound of the invention is used as base oil of lubricant or grease, an additive for lubricant or grease may be blended with the compound as needed. Examples of the additives include an antioxidant, a rust inhibitor, a solid lubricant, a filler, an oiliness agent, a metal deactivator, a water resisting agent, an extreme pressure agent, an anti-wear agent, a viscosity index improver, a coloring agent and a viscosity modifier.

Examples of the extreme pressure agent include: zinc dialkyldithiophosphate; molybdenum dialkyldithiophosphate; thiocarbamates such as ashless dithiocarbamate, zinc dithiocarbamate and molybdenum dithiocarbamate; sulfur compounds such as sulfurized fat and oil, olefin sulfide, polysulfide, sulfurized mineral oil, thiophosphates, thioterpenes and dialkyl thiodipropionates; phosphates and phosphites such as tricrezylphosphates and triphenylphosphites. Examples of the oiliness agent include alcohols, carboxylic acids, glycerides and esters. The contents of these compounds are preferably approximately in a range from 0.1 mass % to 5 mass % of the total amount of the lubricant or grease.

Examples of the antioxidant include: an amine antioxidant such as alkylated diphenylamine, phenyl-α-naphthylamine and alkylated phenyl-α-naphthylamine; a phenolic antioxidant such as 2,6-di-t-butyl-4-methylphenol and 4,4'-methylenebis(2,6-di-t-butylphenol); and a peroxide decomposer such as a sulfuric peroxide decomposer and ZnDTP, which are typically used in a range from 0.05 mass % to 10 mass %.

Examples of the rust inhibitor include benzotriazole, zinc stearate, succinate, succinic acid derivative, thiadiazole, benzotriazole, benzotriazole derivative, sodium nitrite, petroleum sulphonate, sorbitan monooleate, fatty acid soap and an amine compound.

Examples of the solid lubricant include polyimide, PTFE, graphite, metal oxide, boron nitride, melamine cyanurate (MCA) and molybdenum disulfide.

As the viscosity modifier, the lubricant base oil such as DIOA (diisooctyl adipate) and DIDA (diisodecyl adipate) may be mixed approximately in a range of 1 mass % to 30 mass % in use.

Second Exemplary Embodiment

The ester compound in the second exemplary embodiment is an alkylmonoetheralkylmonoester compound of 2,4-diethyl-1,5-pentanediol represented by the following formula (3).

[Formula 8]

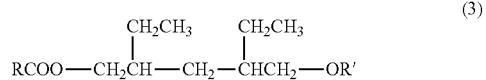

In the formula (3), R and R' independently represent an alkyl group having 5 to 18 carbon atoms. When the number of the carbon atoms of the alkyl group R is 4 or less, a viscosity index may be decreased. When hydrolysis occurs by any chance, short-chain fatty acid may be generated to cause corrosion.

On the other hand, when the number of the carbon atoms of the alkyl group R is 19 or more, kinematic viscosity may be increased to deteriorate fluidity in a low temperature region, occasionally resulting in solidification. Accordingly, the alkyl group R particularly preferably has 6 to 16 carbon atoms.

When the number of the carbon atoms of the alkyl group R' is 4 or less, the viscosity index may be decreased. On the other hand, when the number of the carbon atoms of the alkyl group R' is 19 or more, the viscosity index may be decreased and vaporizability in a high temperature region may be increased.

Accordingly, the alkyl group R' particularly preferably has 6 to 16 carbon atoms.

Further, the total carbon atoms of the compound of the formula (3) are preferably in a range of 24 to 40. When the total carbon atoms are 23 or less, the viscosity index may be decreased and vaporizability in a high temperature region may be increased. On the other hand, when the total carbon atoms are 41 or more, kinematic viscosity may be increased to deteriorate fluidity in a low temperature region, occasionally resulting in solidification. Accordingly, the total carbon atoms are particularly preferably in a range of 26 to 36.

The aforementioned compound of the formula (3) can be easily manufactured, for instance, through an intermediate represented by the following formula (4).

[Formula 9]

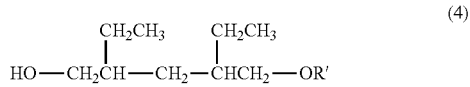

(4)

The intermediate (5-alkoxy-2,4-diethyl-1-pentanol) represented by the formula (4) can be manufactured by heating 2,4-diethyl-1,5-pentanediol and alkyl bromide with stirring in a concentrated alkali solution in the presence of a phase transfer catalyst. Preferable reaction conditions and identification method are as follows:

Temperature: 40 to 95 degrees C. (more preferably 60 to 80 degrees C.);

Time: 1 to 24 hours (preferably about 8 hours);

Catalyst: phase transfer catalyst (tetrabutyl ammonium bromide, tetraisopropyl ammonium bromide and the like);

Solvent: aqueous sodium hydroxide of a concentration of 48 mass % or more, to which solid sodium hydroxide may be added during reaction; and Identification: transition of the reaction can be checked by gas chromatography.

The structure can be identified in more detail by mass analysis, NMR analysis, IR analysis and the like.

A mixture of monoether and diether obtained by the above method is subjected to distilled separation to obtain monoether (intermediate). The monoether is used in manufacturing the compound of the formula (3).

Specifically, 5-alkoxy-2,4-diethyl-1-pentanol and alkyl carboxylic acid are heated with stirring in the presence of an acid catalyst to perform an esterification reaction, in which the generated water only needs to be eliminated.

Moreover, the compound of the formula (3) can be also obtained in a good yield by reacting this ether alcohol and alkyl carboxylic acid chloride in the presence of a base at the room temperature.

Although both of the compounds obtained in the reaction include impurities, the compounds can preferably be as lubricant base oil or grease base oil by being subjected to distillation.

Two preferable examples of the esterification reaction are described as follows.

Reaction of Alcohol (the Formula (4)) and Alkyl Carboxylic Acid

Temperature: 100 to 190 degrees C. (preferably 120 to 180 degrees C.);

Time: 1 to 24 hours (more preferably about 8 hours);

Catalyst: sulfuric acid, titanic acid tetrabutyl, titanic acid tetraisopropyl and titanic acid tetraethyl;

Solvent: toluene, xylene, trimethylbenzene and the like;

Reactor: dehydration using a Dean-Stark apparatus

Identification: transition of the reaction can be checked by gas chromatography.

The structure can be identified by mass analysis, NMR analysis, IR analysis and the like.

Reaction of Alcohol (the Formula (4)) and Alkyl Carboxylic Acid Chloride

Temperature: 10 to 60 degrees C. (more preferably 20 to 40 degrees C.);

Time: 1 to 24 hours (more preferably about 4 hours);

Base: N,N-dimethylaniline, triethylamine and the like;

Solvent: tetrahydrofuran, dibutylether, dimethylether and the like;

Identification: transition of the reaction can be checked by gas chromatography.

The structure can be identified by mass analysis, NMR analysis, IR analysis and the like.

The aforementioned compound of the formula (3) exhibits a high viscosity index and an excellent low-temperature fluidity. Accordingly, the ester compound is useful as base oil of lubricant and is suitably usable as lubricant for an oil-impregnated bearing or an fluid dynamic bearing. Moreover, the compound of the formula (3) is also useful as grease base oil and grease including or provided by blending the grease base oil.

When the compound of the invention is used as base oil of lubricant or grease, an additive for lubricant or grease may be blended with the compound as needed. Examples of the additives include an antioxidant, a rust inhibitor, a solid lubricant, a filler, an oiliness agent, a metal deactivator, a water resisting agent, an extreme pressure agent, an anti-wear agent, a viscosity index improver, a coloring agent and a viscosity modifier.

Examples of the extreme pressure agent include: zinc dialkyldithiophosphate; molybdenum dialkyldithiophosphate; thiocarbamates such as ashless dithiocarbamate, zinc dithiocarbamate and molybdenum dithiocarbamate; sulfur compounds (sulfurized fat and oil, olefin sulfide, polysulfide, sulfurized mineral oil, thiophosphates, thioterpenes, dialkyl thiodipropionates and the like); phosphates and phosphites (tricrezylphosphates, triphenylphosphites and the like). Examples of the oiliness agent include alcohols, carboxylic acids, glycerides and esters. The contents of these compounds are preferably approximately in a range from 0.1 mass % to 5 mass % of the total amount of the lubricant or grease.

Examples of the antioxidant include: an amine antioxidant such as alkylated diphenylamine, phenyl-α-naphthylamine and alkylated phenyl-α-naphthylamine; a phenolic antioxidant such as 2,6-di-t-butyl-4-methylphenol and 4,4'-methylenebis(2,6-di-t-butylphenol); and a peroxide decomposer such as a sulfuric peroxide decomposer and ZnDTP, which are typically used in a range from 0.05 mass % to 10 mass %.

Examples of the rust inhibitor include benzotriazole, zinc stearate, succinate, succinic acid derivative, thiadiazole, benzotriazole, benzotriazole derivative, sodium nitrite, petroleum sulphonate, sorbitan monooleate, fatty acid soap and an amine compound.

Examples of the solid lubricant include polyimide, PTFE, graphite, metal oxide, boron nitride, melamine cyanurate (MCA) and molybdenum disulfide.

As the viscosity modifier, the lubricant base oil such as DIOA (diisooctyl adipate) and DIDA (diisodecyl adipate) may be mixed approximately in a range of 1 mass % to 30 mass % in use.

EXAMPLES

Next, the invention will be further described in detail with reference to Examples and Comparatives, the description of which by no means limits scope of the invention.

Example 1

Table 1 shows examples and properties of manufacturing intermediate bodies obtained by the method described above in the first exemplary embodiment.

TABLE 1

| Signs | Name of Compounds | Kinematic Viscosity @40° C. (mm$^2$/s) | Kinematic Viscosity @100° C. (mm$^2$/s) | Viscosity Index (VI) |
|---|---|---|---|---|
| Intermediate 1-1 | 2,2-bis(octyloxymethyl)butane-1-ol | 13.47 | 2.887 | 34 |
| Intermediate 1-2 | 2,2-bis(nonyloxymethyl)butane-1-ol | 16.00 | 3.330 | 61 |
| Intermediate 1-3 | 2,2-bis(decyloxymethyl)butane-1-ol | 20.04 | 3.846 | 68 |

A specific manufacturing method of an intermediate 1-2 will be exemplarily described below.

Manufacture of 2,2-bis(nonyloxymethyl)butane-1-ol

Under nitrogen stream, to a 2-L reactor provided with a stirrer, thermometer, condenser and gas inlet tube, 107.3 g (0.8 mol) of trimethylolpropane and 249 g (1.2 mol) of n-nonyl bromide and 11.4 g of tetrabutyl ammonium bromide were put, to which 360 g of 50 mass/volume % aqueous sodium hydroxide was added and heated at 70 to 80 degrees C. for four hours with stirring. After the reaction, the mixture was cooled and left still overnight to deposit white crystal. A liquid layer is transferred to a separating funnel by decantation. An alkali layer of an under layer was removed by separation. An organic layer was washed with 400 mL of saturated saline and 50 mL of a dilute aqueous solution of sulfuric acid. After the organic layer was further washed with distilled water until becoming neutral, 190 g of the obtained organic layer was dried with magnesium sulfate.

After being put through a column layer of 50-g silica gel, the organic layer was subjected to vacuum distillation to be fractioned. The obtained fraction was subjected to mass analysis, NMR analysis and IR analysis, whereby the fraction was confirmed to be 2,2-bis(nonyloxymethyl)butane-1-ol (target compound) (mass analysis result: m/z=386). The obtained amount was 110 g (0.28 mol) (a yield of 47%).

Figure 2:
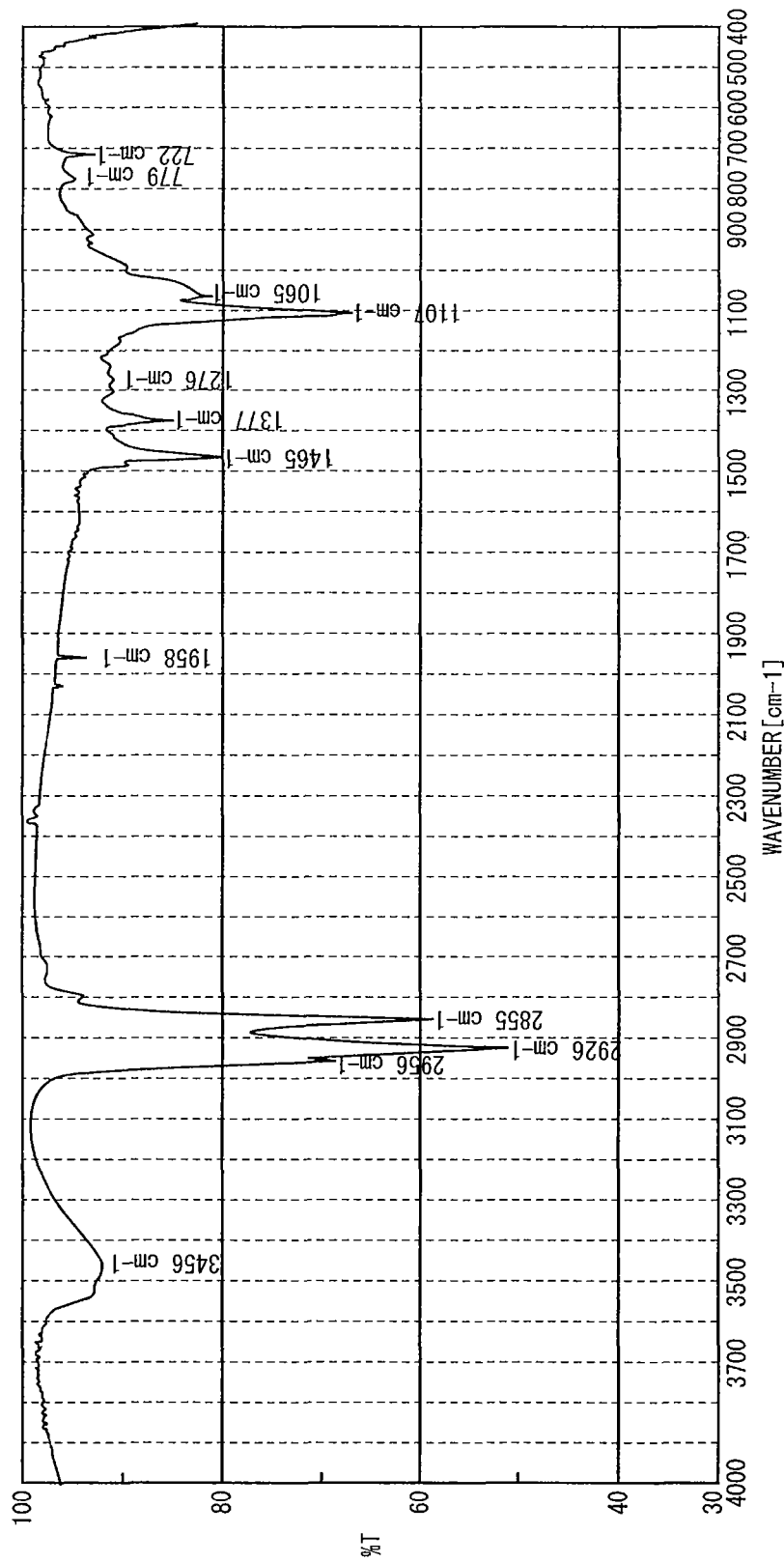
FIG. 2 shows an IR chart of 2,2-bis(nonyloxymethyl)butane-1-ol (intermediate) in Example 1.

FIG. 1 shows a $^1$H NMR chart of this compound. FIG. 2 shows an IR chart thereof Table 2 shows properties of the compound of the formula (2) obtained by the method described above in the above exemplary embodiment and a diester compound for comparison.

TABLE 2

| Signs | Name of Compounds | Kinematic Viscosity @40° C. (mm$^2$/s) | Kinematic Viscosity @100° C. (mm$^2$/s) | Viscosity Index (VI) | State −40° C. |
|---|---|---|---|---|---|
| Compound 1-1 | decanoic acid 2,2-bis(octyloxymethyl)butyl ester | 14.26 | 3.622 | 143 | liquid |
| Compound 1-2 | decanoic acid 2,2-bis(nonyloxymethyl)butyl ester | 16.29 | 4.002 | 150 | liquid |
| Comparison Compound 1-1 | 1-nonyloxy-2,2-bis(nonyloxymethyl)butane | 13.71 | 3.560 | 148 | no fluidity |
| Comparison Compound 1-2 | 1-nonyloxy-2,2-bis(decyloxymethyl)butane | 15.13 | 3.856 | 156 | no fluidity |
| Comparison Compound 1-3 | heptanoic acid triester of trimethylolpropane | 13.72 | 3.416 | 127 | liquid |
| Comparison Compound 1-4 | mixed ester of heptanoic acid and octanoic acid of trimethylolpropane | 15.52 | 3.706 | 128 | liquid |
| Comparison Compound 1-5 | octanoic acid triester of trimethylolpropane | 17.59 | 3.997 | 127 | liquid |
| Comparison Compound 1-6 | 2-ethyl hexanoic acid triester of trimethylolpropane | 24.16 | 4.300 | 70 | no fluidity |

A specific manufacturing method of a compound 1-2 will be exemplarily described below.

Manufacture of Decanoic Acid
2,2-bis(nonyloxymethyl)butyl Ester

To a 1-L three-neck flask provided with a stirrer, thermometer, condenser and dropping funnel with a gas inlet tube, 73.4 g (0.19 mol) of 2,2-bis(nonyloxymethyl)butane-1-ol, 26.7 g (0.22 mol) of N,N-dimethylaniline and 150 mL of tetrahydrofuran were put, to which 38.1 g (0.2 mol) of decanoyl chloride was dropped and stirred at the room temperature under nitrogen stream. After the dropping, the mixture was heated to 45 degrees C. and stirred for five hours. After the reaction, a small amount of distilled water was added to the mixture to dissolve the generated white solid. The mixture was transferred to a separating funnel. After an aqueous layer was separated while an organic layer was added with 50 mL of tetrahydrofuran, washed with 200 mL of saturated saline and with 20 mL of dilute sulfuric acid and then washed with distilled water until the organic layer became neutral. The obtained organic layer was dried with magnesium sulfate. After the solvent was removed by an evaporator, 100 g of the mixture was subjected to vacuum distillation to be fractioned. The obtained fraction was subjected to mass analysis, NMR analysis and IR analysis, whereby the fraction was confirmed to be an ester (target compound) (mass analysis result: m/z=540). The obtained amount was 61.8 g (0.114 mol) (a yield of 60%).

Figure 3:
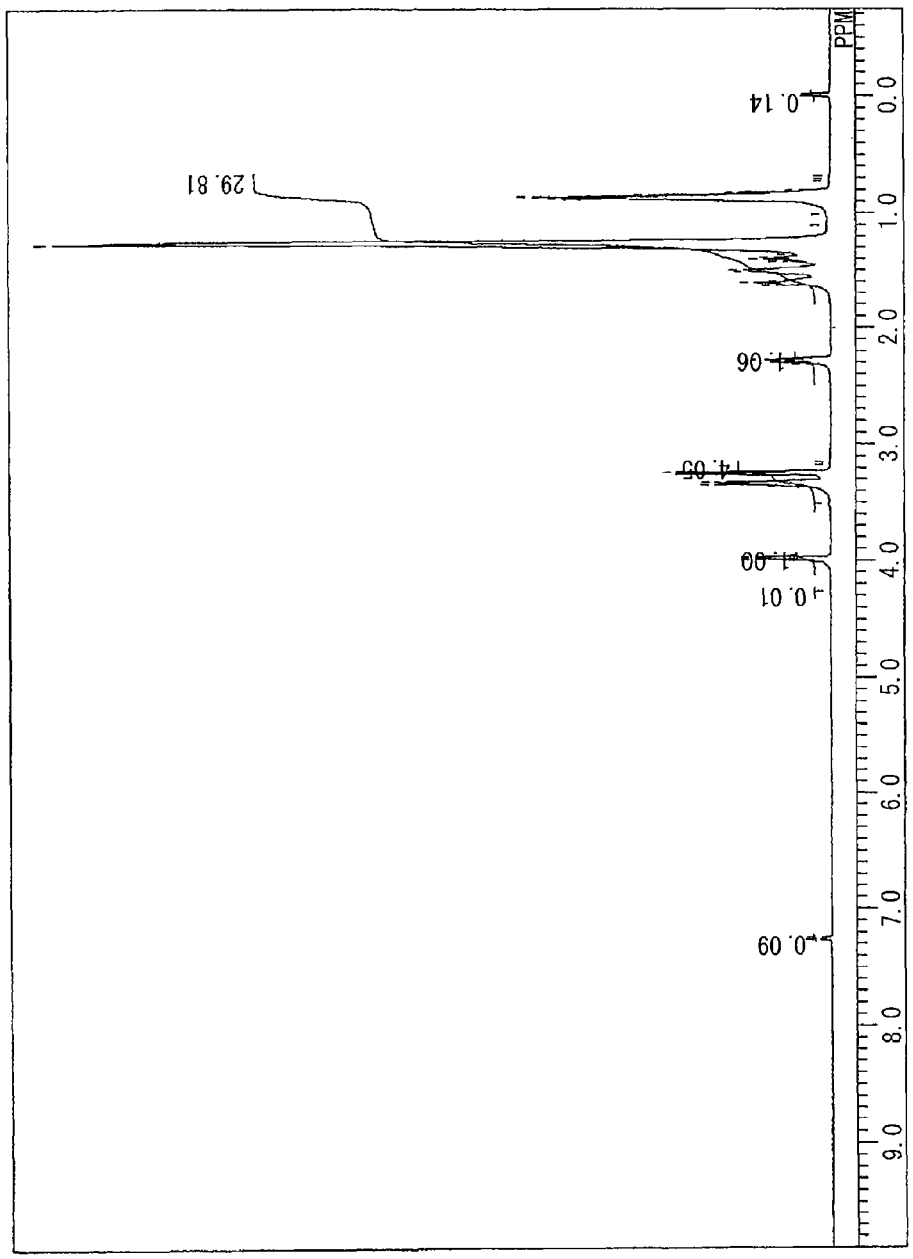
FIG. 3 shows a $^1$H NMR chart of decanoic acid 2,2-bis(nonyloxymethyl)butyl ester in Example 1.
Figure 4:
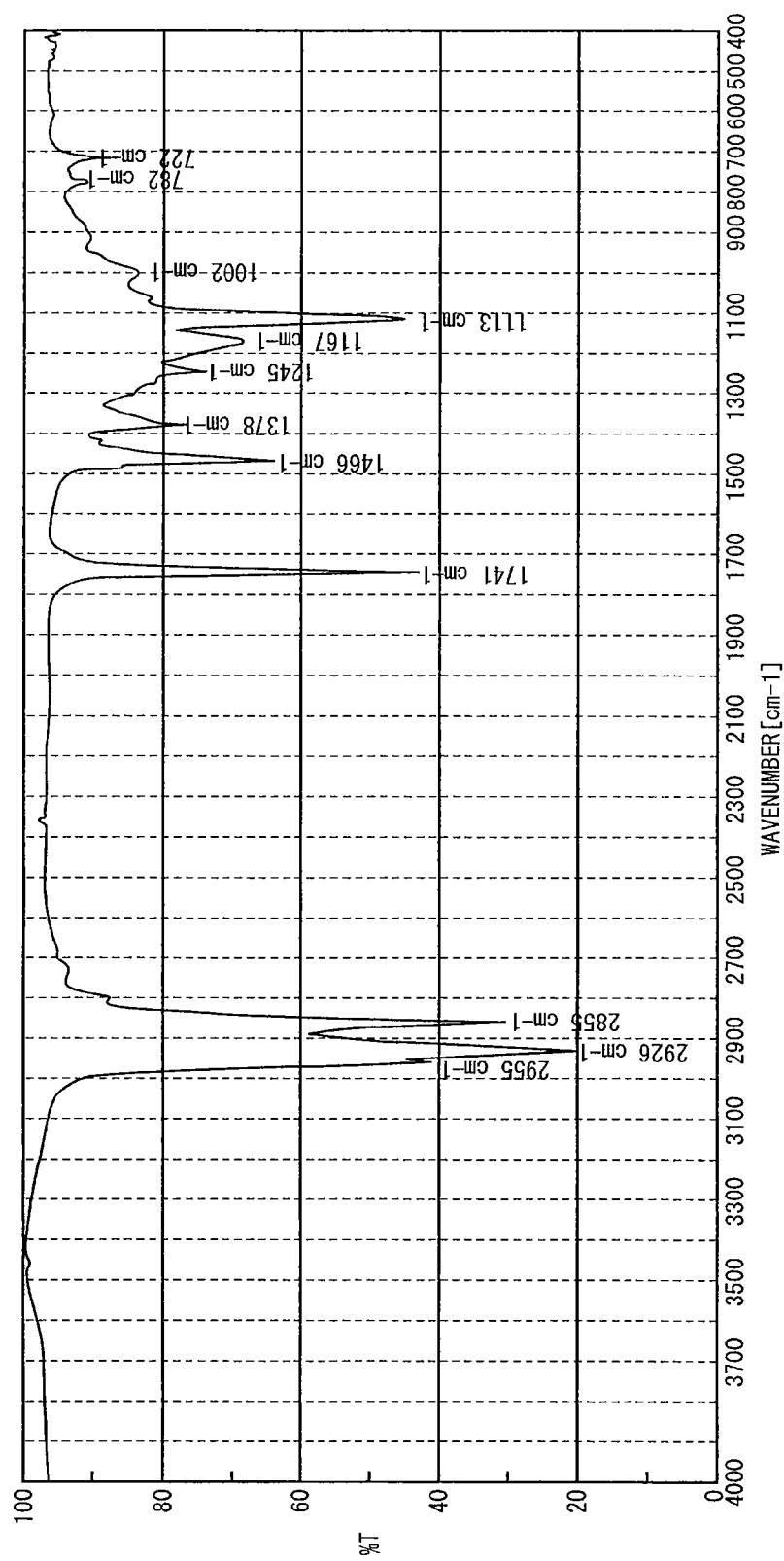
FIG. 4 shows an IR chart of decanoic acid 2,2-bis(nonyloxymethyl)butyl ester in Example 1.

FIG. 3 shows a $^1$H NMR chart of this compound. FIG. 4 shows an IR chart thereof.

It is understood from Table 2 that, in comparison between the compound of the invention and the comparative compound not having a predetermined structure of the invention, the compound of the invention exhibits a higher viscosity index and more excellent low-temperature fluidity than the comparative compound. Accordingly, it can be also understood that the compound of the invention is useful as base oil for lubricant and grease.

Example 2

Table 3 shows examples and properties of a manufacturing intermediate of the formula (4) obtained by the method described above in the second exemplary embodiment.

A specific manufacturing method of an intermediate 2-3 will be exemplarily described below.

Manufacture of 5-nonyloxy-2,4-diethyl-1-pentanol

Under nitrogen stream, to a 2-L reactor provided with a stirrer, thermometer, condenser and gas inlet tube, 320 g (2 mol) of 2,4-diethyl-1,5-pentanediol, 311 g (1.5 mol) of n-nonylbromide and 12 g of tetrabutylammonium bromide were put, to which 532 g of 52 mass/volume % aqueous sodium hydroxide was added and heated at 70 to 80 degrees C. for six hours with stirring. After the reaction, the mixture was cooled and left still overnight to deposit white crystal. A liquid layer is transferred to a separating funnel by decantation. The white crystal was washed with 20 mL of hexane. The washing liquid of hexane was added to the liquid layer.

An alkali layer of an under layer was removed by separation. An organic layer was washed with 500 mL of saturated saline and 100 mL of a dilute aqueous solution of sulfuric acid. After the organic layer was further washed with distilled water until becoming neutral, the obtained organic layer was dried with magnesium sulfate.

After being put through a column layer of 50-g silica gel, the organic layer was subjected to vacuum distillation to be fractioned. The obtained fraction was subjected to mass analysis, NMR analysis and IR analysis, whereby the fraction was confirmed to be 5-nonyloxy-2,4-diethyl-1-pentanol (target compound) (mass analysis result: m/z=286). The obtained amount was 284 g (a yield of 66%). A main component of a distillation residue was 1,5-dinonyloxy-2,4-diethyl-1-pentane.

Figure 5:
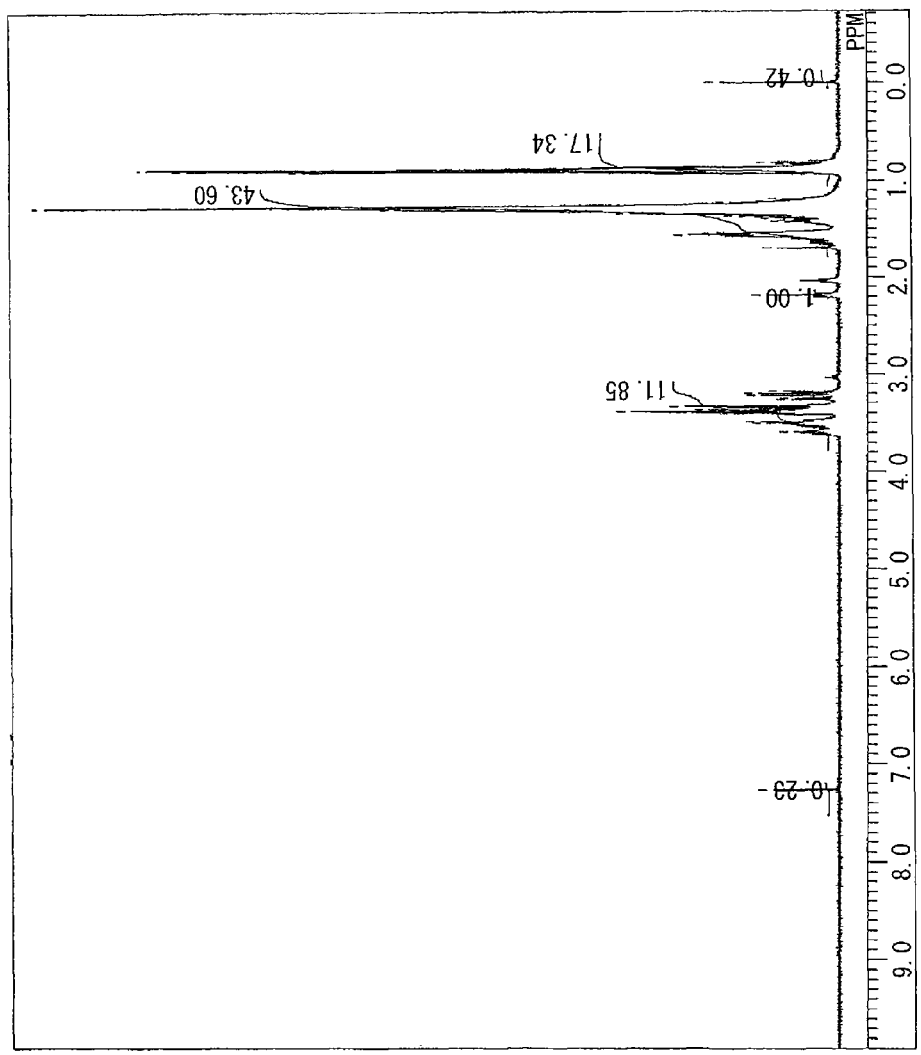
FIG. 5 shows a $^1$HNMR chart of 5-nonyloxy-2,4-diethyl-1-pentanol (intermediate) in Example 2.
Figure 6:
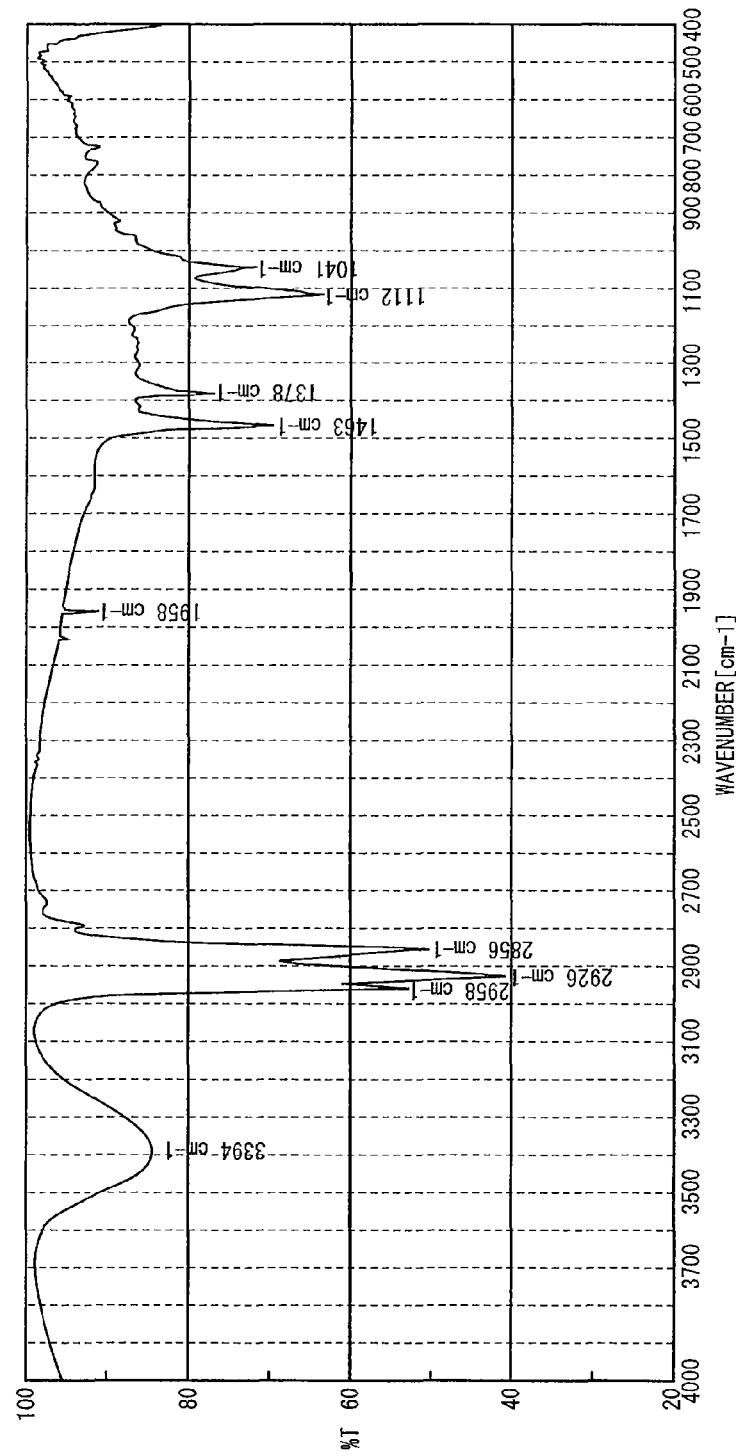
FIG. 6 shows an IR chart of 5-nonyloxy-2,4-diethyl-1-pentanol (intermediate) in Example 2.

FIG. 5 shows a $^1$H NMR chart of this compound. FIG. 6 shows an IR chart thereof Table 4 shows properties of the monoester compound of the formula (3) obtained by the method described above in the above exemplary embodiment and a diester compound for comparison.

TABLE 3

| Signs | Name of Compounds | Kinematic Viscosity | | Viscosity Index (VI) |
| --- | --- | --- | --- | --- |
| | | @40° C. (mm$^2$/s) | @100° C. (mm$^2$/s) | |
| Intermediate 2-1 | 5-(2-ethylhexyloxy)-2,4-diethyl-1-pentanol | 18.91 | 2.616 | −254 |
| Intermediate 2-2 | 5-octyloxy-2,4-diethyl-1-pentanol | 16.70 | 2.666 | −148 |
| Intermediate 2-3 | 5-nonyloxy-2,4-diethyl-1-pentanol | 17.44 | 2.859 | −103 |
| Intermediate 2-4 | 5-decyloxy-2,4-diethyl-1-pentanol | 19.73 | 3.037 | −115 |
| Intermediate 2-5 | 5-undecyloxy-2,4-diethyl-1-pentanol | 21.81 | 3.382 | −69 |
| Intermediate 2-6 | 5-dodecyloxy-2,4-diethyl-1-pentanol | 23.70 | 3.643 | −46 |

TABLE 4

| Signs | Name of Compounds | Kinematic Viscosity @40° C. (mm²/s) | @100° C. (mm²/s) | Viscosity Index (VI) | State −40° C. |
|---|---|---|---|---|---|
| Compound 2-1 | n-octanoic acid 5-octyloxy-2,4-diethyl-1-pentylester | 8.06 | 2.314 | 129 | liquid |
| Compound 2-2 | n-decanoic acid 5-octyloxy-2,4-diethyl-1-pentylester | 9.87 | 2.833 | 141 | liquid |
| Compound 2-3 | n-dodecanoic acid 5-octyloxy-2,4-diethyl-1-pentylester | 12.09 | 3.291 | 150 | liquid |
| Compound 2-4 | n-dodecanoic acid 5-nonyloxy-2,4-diethyl-1-pentylester | 13.10 | 3.479 | 151 | liquid |
| Compound 2-5 | 2-butyloctanoic acid 5-decyloxy-2,4-diethyl-1-pentylester | 14.99 | 3.536 | 116 | liquid |
| Compound 2-6 | 2-hexyldecanoic acid 5-octyloxy-2,4-diethyl-1-pentylester | 16.38 | 3.796 | 124 | liquid |
| Compound 2-7 | isotridecanoic acid 5-decyloxy-2,4-diethyl-1-pentylester | 17.86 | 4.063 | 130 | liquid |
| Compound 2-8 | 2-octyldecanoic acid 5-octyloxy-2,4-diethyl-1-pentylester | 18.06 | 4.114 | 132 | liquid |
| Comparative Compound 2-1 | n-octanoic acid diester of 2,4-diethyl-1,5-pentanediol | 9.75 | 2.745 | 129 | liquid |
| Comparative Compound 2-2 | n-decanoic acid diester of 2,4-diethyl-1,5-pentanediol | 13.87 | 3.577 | 146 | no fluidity |
| Comparative Compound 2-3 | n-dodecanoic acid diester of 2,4-diethyl-1,5-pentanediol | 18.41 | 4.375 | 154 | no fluidity |

A specific manufacturing method of a compound 2-4 will be exemplarily described below.

Manufacture of Dodecanoic Acid 5-nonyloxy-2,4-diethyl-1-pentylester

To a 1-L three-neck flask provided with a stirrer, thermometer, condenser and dropping funnel with a gas inlet tube, 260 g (0.91 mol) of 5-nonyloxy-2,4-diethyl-1-pentanol, 112 g (0.92 mol) of N,N-dimethylaniline and 150 mL of tetrahydrofuran were put, to which 197 g (0.9 mol) of decanoyl chloride was dropped and stirred at the room temperature under nitrogen stream. After the dropping, the mixture was heated to 45 degrees C. and stirred for four hours. After the reaction, a small amount of distilled water was added to the reactant to dissolve the generated white solid. The reactant was transferred to a separating funnel. After an aqueous layer was separated while an organic layer was added with 150 mL of tetrahydrofuran, washed with 300 mL of saturated saline and with 20 mL of dilute sulfuric acid and then washed with distilled water until the organic layer became neutral. The obtained organic layer was dried with magnesium sulfate. After the solvent was removed by an evaporator, the organic layer was subjected to vacuum distillation to be fractioned. The obtained fraction was subjected to mass analysis, NMR analysis and IR analysis, whereby the fraction was confirmed to be a monoester compound (target compound) (mass analysis result: m/z=468). The obtained amount was 185 g (a yield of 43%).

Figure 7:
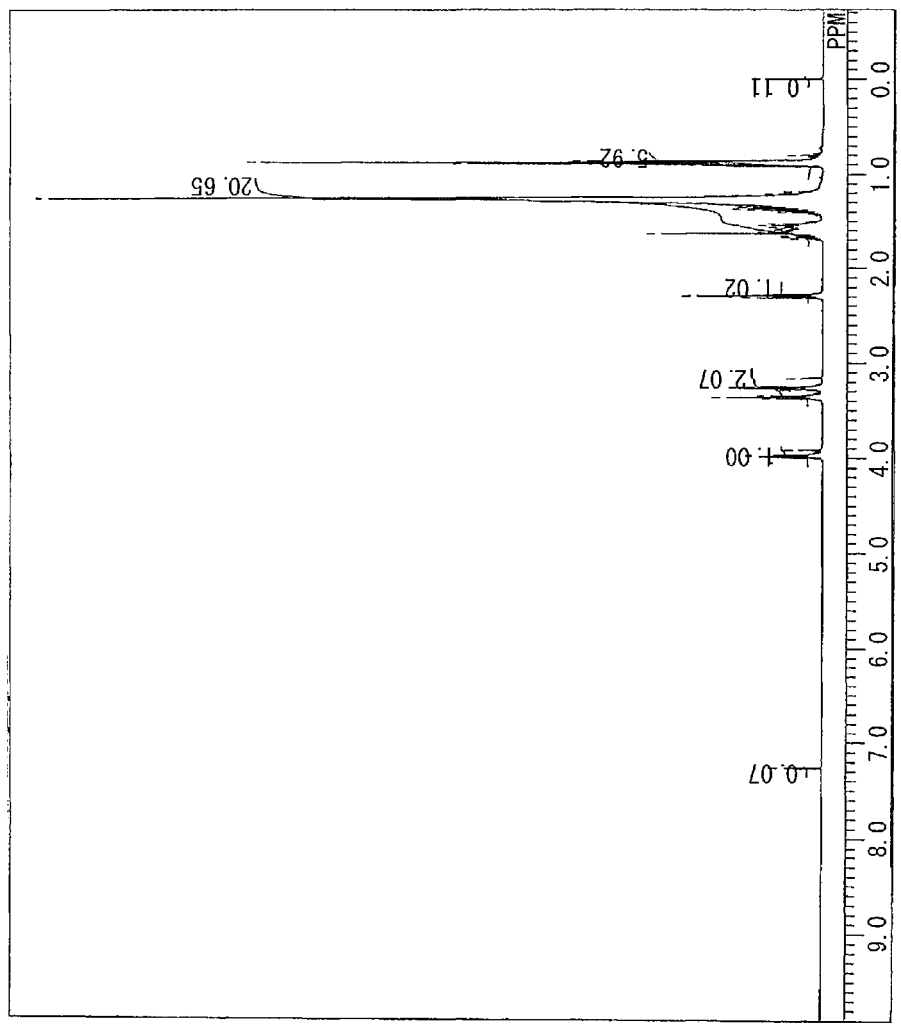
FIG. 7 shows a $^1$HNMR chart of dodecanoic acid 5-nonyloxy-2,4-diethyl-1-pentyl ester in Example 2.
Figure 8:
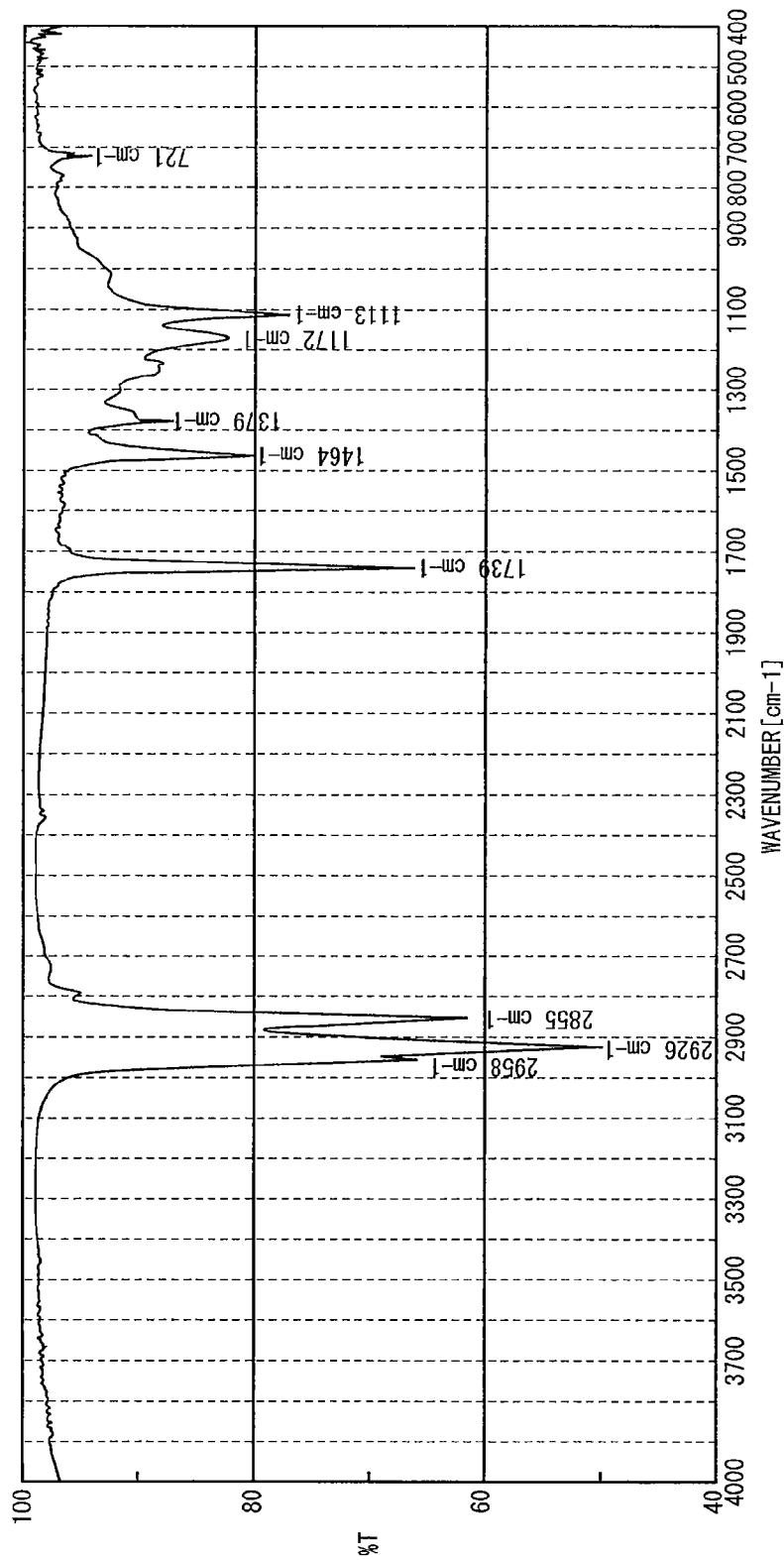
FIG. 8 shows an IR chart of dodecanoic acid 5-nonyloxy-2,4-diethyl-1-pentyl ester in Example 2.

FIG. 7 shows a ¹H NMR chart of this compound. FIG. 8 shows an IR chart thereof

It is understood from Table 4 that, in comparison between the compound (monoester) of the invention and the comparative compound (diester), when both of the compound and the comparative compound have a kinematic viscosity at the same level, the compound of the invention exhibits a higher viscosity index and more excellent low-temperature fluidity than the comparative compound. Accordingly, it is also understood that the compound of the invention is useful as base oil for lubricant and grease.

The invention claimed is:

1. An ester compound according to formula (2):

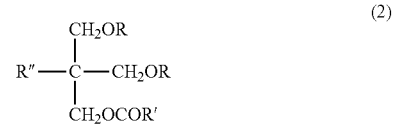

(2)

wherein:
each of R and R' independently represents an alkyl group having 5 to 18 carbon atoms; and
R" represents hydrogen or an alkyl group having at most 5 carbon atoms.

2. The ester compound according to claim 1, wherein a total number of carbon atoms in the ester compound is 24 to 42.

3. The ester compound according to claim 1, wherein R" represents an ethyl group or a propyl group.

4. A lubricant base oil, comprising the ester compound according to claim 1.

5. A lubricant, comprising the lubricant base oil according to claim 4.

6. The lubricant according to claim 5, wherein the lubricant is suitable for an oil-impregnated bearing or a fluid dynamic bearing.

7. A grease base oil, comprising the ester compound according to claim 1.

8. A grease, comprising the grease base oil according to claim 7.

9. An ester compound according to formula (3):

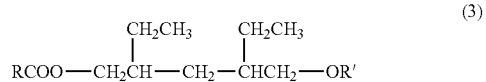

(3)

wherein:
each of R and R' independently represents an alkyl group having 5 to 18 carbon atoms; and
a total number of carbon atoms in the ester compound is 24 to 40.

10. A lubricant base oil, comprising the ester compound according to claim 9.

11. A lubricant, comprising the lubricant base oil according to claim 10.

12. The lubricant according to claim 11, wherein the lubricant is suitable for an oil-impregnated bearing or a fluid dynamic bearing.

13. A grease base oil, comprising the ester compound according to claim 9.

14. A grease, comprising the grease base oil according to claim 13.

15. A manufacturing intermediate

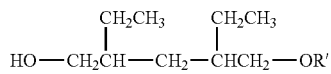
(4)

selected from the group consisting of 5-(2-ethylhexyloxy)-2,4-diethyl-1-pentanol, 5-nonyloxy-2,4-diethyl-1-pentanol, 5-decyloxy-2,4-diethyl-1-pentanol, 5-undecyloxy-2,4-diethyl-1-pentanol, and 5-dodecyloxy-2,4-diethyl-1-pentanol.

* * * * *